US008361048B2

(12) United States Patent
Kuen et al.

(10) Patent No.: US 8,361,048 B2
(45) Date of Patent: Jan. 29, 2013

(54) REFASTENABLE ABSORBENT PRODUCT WITH OVERLAID SIDE PANELS AND METHOD OF MAKING SAME IN THE MACHINE DIRECTION

(75) Inventors: David Arthur Kuen, Neenah, WI (US);
Robert Lee Popp, Hortonville, WI (US);
Joseph D. Coenen, Neenah, WI (US);
Shawn A. Quereshi, Neenah, WI (US);
Jack L. Couillard, Menasha, WI (US);
Christopher Peter Olson, Neenah, WI (US)

(73) Assignee: Kimberly-Clark Worldwide, Inc.,
Neenah, WI (US)

( * ) Notice: Subject to any disclaimer, the term of this patent is extended or adjusted under 35 U.S.C. 154(b) by 1418 days.

(21) Appl. No.: 10/457,224

(22) Filed: Jun. 9, 2003

(65) Prior Publication Data
US 2003/0212378 A1 Nov. 13, 2003

Related U.S. Application Data

(62) Division of application No. 09/815,788, filed on Mar. 23, 2001, now Pat. No. 6,635,135.

(51) Int. Cl.
*A61F 13/15* (2006.01)
*A61F 13/20* (2006.01)
(52) U.S. Cl. ............... 604/387; 604/386; 604/385.11
(58) Field of Classification Search .............. 604/376, 604/385.1, 385.03, 385.11, 386–391, 11, 604/385.01; 156/250, 256
See application file for complete search history.

(56) References Cited

U.S. PATENT DOCUMENTS

| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 4,145,763 A | 3/1979 | Abrams et al. |
| 4,205,679 A | 6/1980 | Repke et al. |
| 4,340,563 A | 7/1982 | Appel et al. |
| 4,402,690 A | 9/1983 | Redfern |
| 4,610,680 A | 9/1986 | LaFleur |
| 4,615,695 A | 10/1986 | Cooper |
| 4,663,220 A | 5/1987 | Wisneski et al. |
| 4,699,622 A | 10/1987 | Toussant et al. |
| 4,704,116 A | 11/1987 | Enloe |

(Continued)

FOREIGN PATENT DOCUMENTS

| EP | 217 032 | 4/1987 |
| EP | 0 650 714 | 5/1995 |

(Continued)

OTHER PUBLICATIONS

"Discrete", Oxford Online dictionary, 2006.*

*Primary Examiner* — Michele M Kidwell
(74) *Attorney, Agent, or Firm* — Dority & Manning, P.A.

(57) ABSTRACT

A prefastened absorbent garment is manufactured with its longitudinal axis in the machine direction. A web of garment chassis material extending in the machine direction is overlaid with a side panel web. The side panel web is attached at opposite width borders of the chassis web and has one or more complementary fasteners opposing each other in the longitudinal axis direction of the garment chassis web. The garment can be folded to place the complementary fasteners in releasable engagement and individuated from the combined chassis and side panel webs.

20 Claims, 8 Drawing Sheets

U.S. PATENT DOCUMENTS

| | | | |
|---|---|---|---|
| 4,940,464 A | 7/1990 | Van Gompel et al. | |
| 5,046,272 A | 9/1991 | Vogt et al. | |
| 5,087,253 A | 2/1992 | Cooper | |
| 5,104,116 A | 4/1992 | Pohjola | |
| 5,224,405 A | 7/1993 | Pohjola | |
| 5,226,992 A | 7/1993 | Morman | |
| 5,370,634 A | 12/1994 | Ando et al. | |
| 5,496,428 A | 3/1996 | Sageser et al. | |
| 5,531,732 A * | 7/1996 | Wood | 604/391 |
| 5,540,796 A | 7/1996 | Fries | |
| 5,580,411 A * | 12/1996 | Nease et al. | 156/260 |
| 5,624,420 A * | 4/1997 | Bridges et al. | 604/365 |
| 5,779,831 A | 7/1998 | Schmitz | |
| 5,785,699 A | 7/1998 | Schmitz | |
| 5,795,350 A | 8/1998 | Schmitz | |
| 5,830,206 A | 11/1998 | Larsson | |
| 5,855,574 A | 1/1999 | Kling et al. | |
| 5,897,545 A | 4/1999 | Kline et al. | |
| 5,961,761 A | 10/1999 | Heindel et al. | |
| 6,036,805 A | 3/2000 | McNichols | |
| 6,287,287 B1 * | 9/2001 | Elsberg | 604/385.03 |
| 6,328,725 B2 | 12/2001 | Fernfors | |
| 6,395,115 B1 | 5/2002 | Popp et al. | |
| 6,409,858 B1 | 6/2002 | Popp et al. | |
| 6,432,243 B1 | 8/2002 | Popp et al. | |
| 6,432,248 B1 | 8/2002 | Popp et al. | |
| 6,447,628 B1 | 9/2002 | Couillard et al. | |
| 6,461,344 B1 | 10/2002 | Widlund et al. | |
| 6,464,679 B1 * | 10/2002 | Hirokawa | 604/390 |
| 6,481,362 B2 | 11/2002 | Hietpas et al. | |
| 6,497,032 B2 | 12/2002 | Maxton et al. | |
| 6,508,797 B1 * | 1/2003 | Pozniak et al. | 604/385.11 |
| 6,513,221 B2 | 2/2003 | Vogt et al. | |
| 6,514,187 B2 | 2/2003 | Coenen et al. | |
| 2001/0042584 A1 | 11/2001 | Karami et al. | |
| 2002/0111596 A1 | 8/2002 | Fletcher et al. | |
| 2002/0138062 A1 | 9/2002 | Kuen et al. | |

FOREIGN PATENT DOCUMENTS

| | | |
|---|---|---|
| EP | 755 238 | 1/1997 |
| EP | 757 550 | 12/1998 |
| EP | 1 110 529 | 6/2001 |
| GB | 1 520 740 | 8/1978 |
| WO | WO 84/04242 | 11/1984 |
| WO | WO 95/18591 | 7/1995 |
| WO | 95/27462 | 10/1995 |
| WO | 97/23180 | 7/1997 |
| WO | WO 97/23180 A1 * | 7/1997 |
| WO | 97/46197 | 12/1997 |
| WO | 00/23025 | 4/2000 |
| WO | 00/35395 | 6/2000 |
| WO | 00/35398 | 6/2000 |
| WO | 00/37009 | 6/2000 |
| WO | WO 0035396 A1 * | 6/2000 |

* cited by examiner

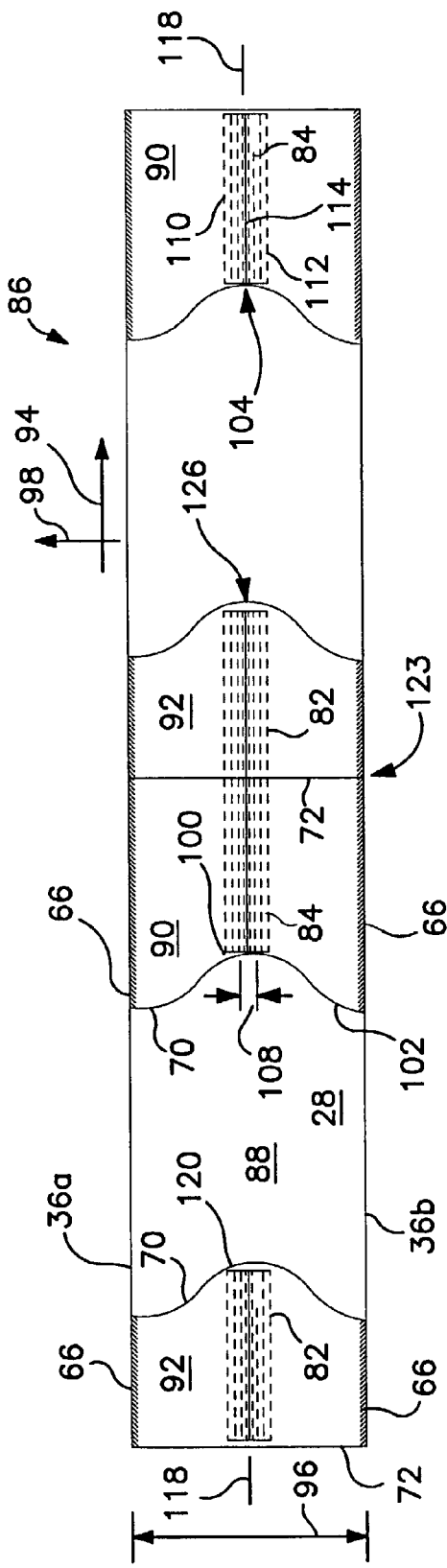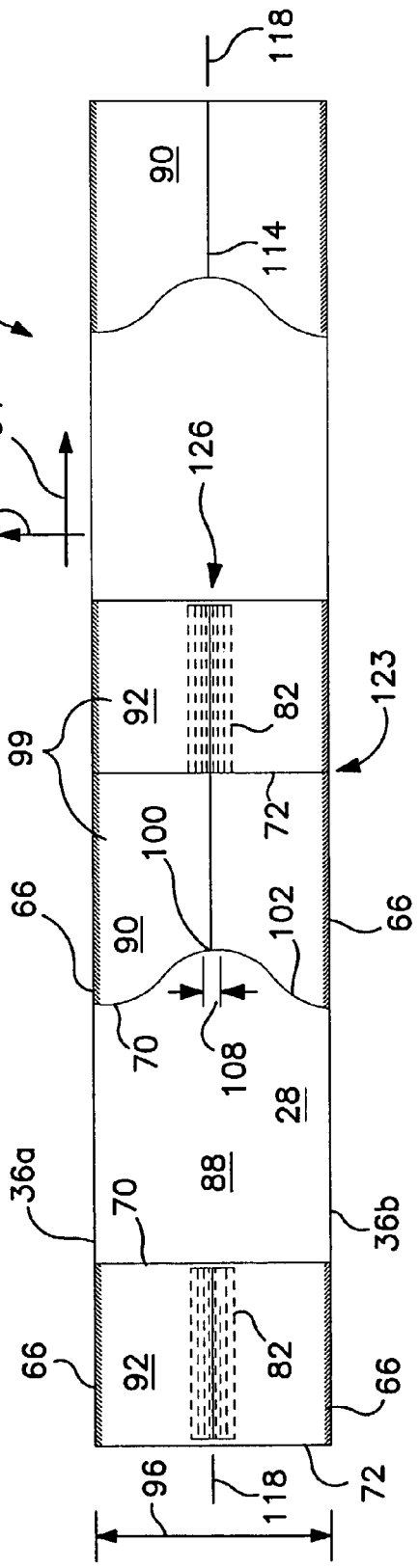
FIG. 4A
FIG. 4B

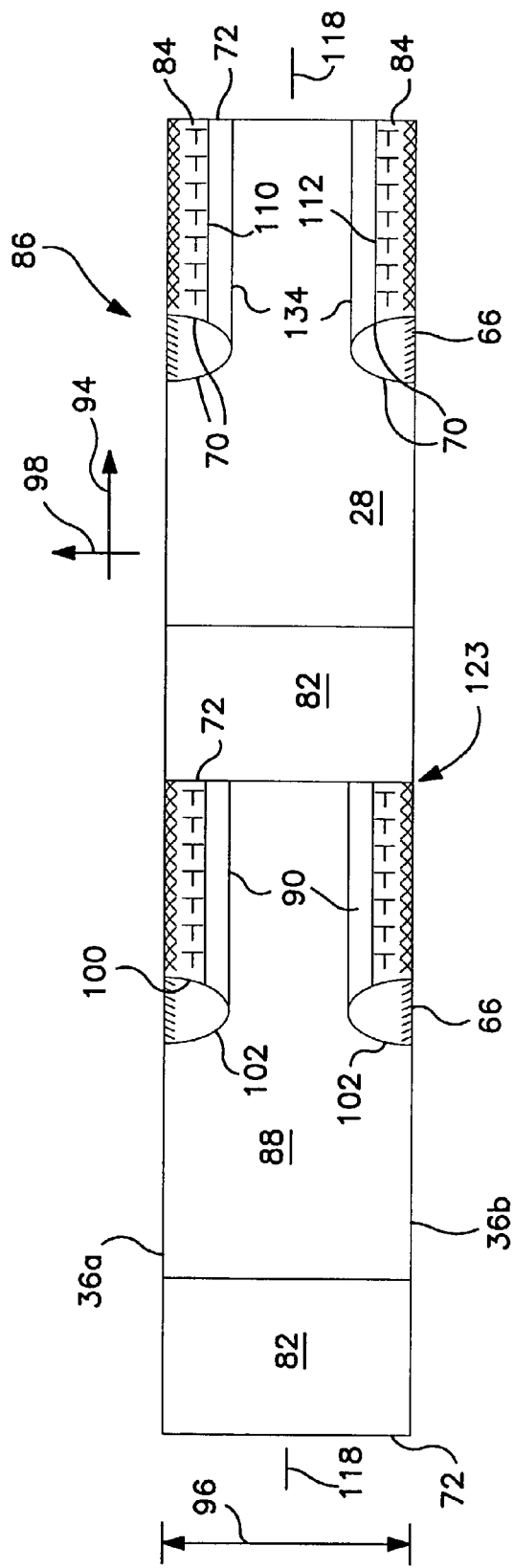
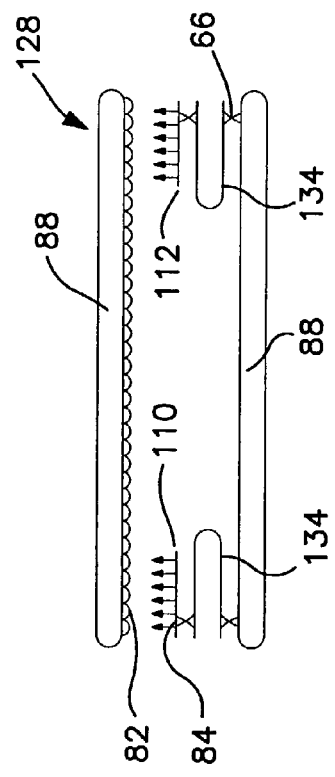
FIG. 4C
FIG. 9

REFASTENABLE ABSORBENT PRODUCT WITH OVERLAID SIDE PANELS AND METHOD OF MAKING SAME IN THE MACHINE DIRECTION

This application is a divisional of U.S. patent application Ser. No. 09/815,788, filed on Mar. 23, 2001 now U.S. Pat. No. 6,635,135.

BACKGROUND OF THE INVENTION

In the known art, there have been two ways of making a garment web into point of sale items. One is to put refastenable tabs, such as adhesive tape or hook and loop combinations onto the garment body, in the manner of an infant diaper, for later use to secure the back panel of the diaper to the front panel. A second is to bond the side edges of the front and back side regions together to make a closed garment, in the manner of a training pant which is slid on and off the wearer like a regular adult garment. To remove such a garment if it becomes soiled, it is necessary to break the side regions in order to remove the garment like a diaper, as convenience and hygiene would dictate.

It is therefore desired to provide a garment, such as a training pant, which may be slid-on in the fashion of an adult underwear while being easily removeable in the manner of a diaper and which can be made with relatively uncomplicated machinery in a space-efficient manner.

SUMMARY OF THE INVENTION

The present invention can provide a readily and inexpensively producible refastenable garment. The garment is desirably manufactured with its longitudinal axis in the machine direction. A generally rectangular web of garment chassis materials extending in the machine direction can be overlaid with side panel webs opposing each other in the machine direction. The side panel webs are attached at opposite upstream and downstream sides of the chassis web and have cooperative fasteners, such as hook and loop fasteners, opposing each other in the machine direction. The side panels do not extend beyond the chassis web, making the manufacturing process very compact. The manufactured garment is also compact and needs only one fold to place it in condition for packaging. The fold places the cooperative fasteners in a fastening relationship. Each fastener element can be through-cut or provided with a line of weakness at its longitudinal axis such that the side panel webs will separate upon opening the garment for use. The side panel webs can be shaped on selected edges to provide an efficacious leg hole fit. The side panel webs can also be extendible or elastic to provide an efficacious garment fit for the manufactured garment.

BRIEF DESCRIPTION OF THE DRAWINGS

These and other objects and features of this invention will be better understood from the following detailed description taken in conjunction with the drawings wherein:

FIGS. 4A, 4B, 4C and 4D show alternative in-process manufactures of the absorbent garment with refastenable side seams according to the present invention.

FIG. 9 illustrates an end view at the waistband area of a garment having a panel with one fastener component disposed on the surface of the chassis web as in FIG. 4C.

DEFINITIONS

Figure 1:
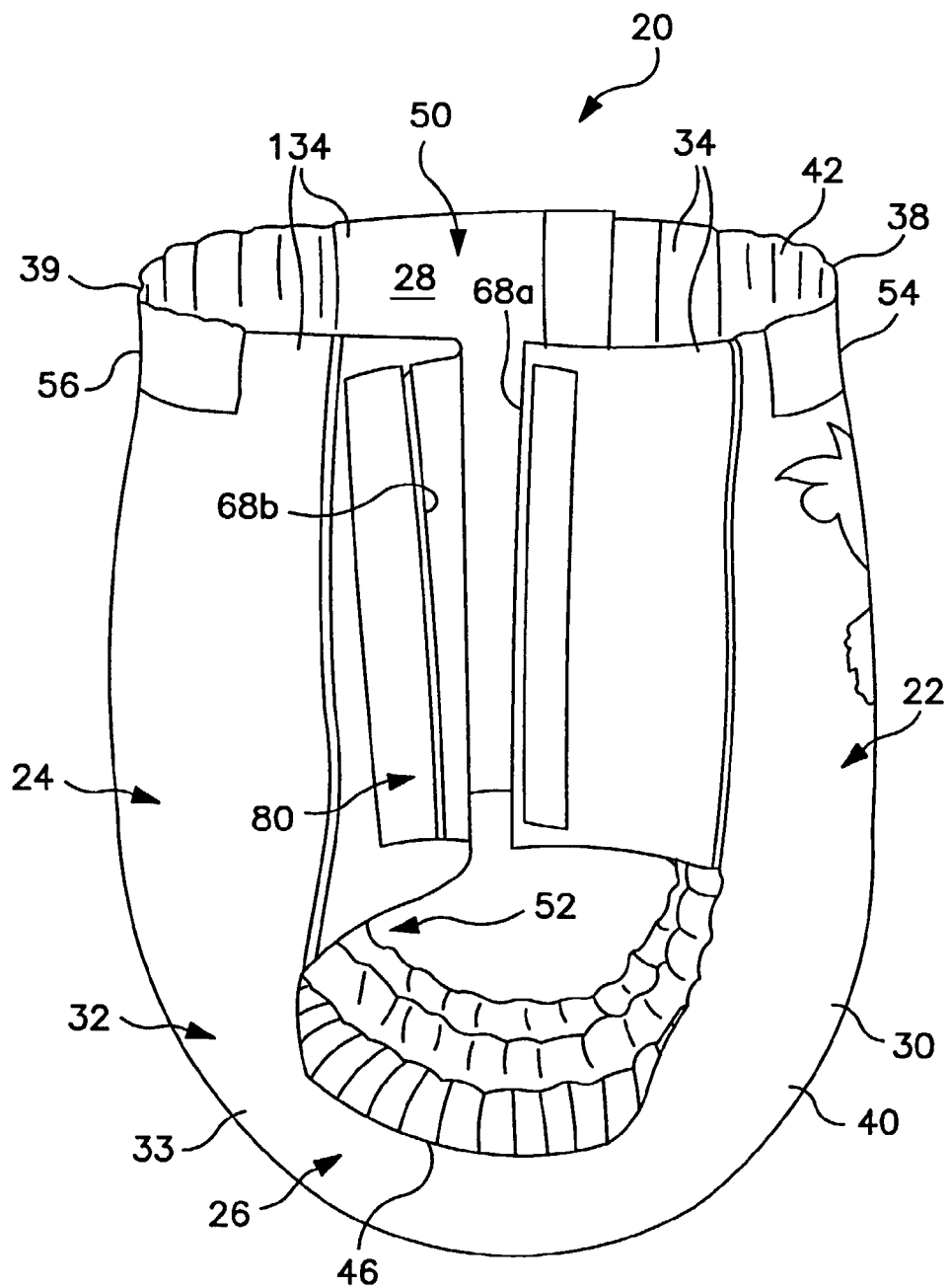
FIG. 1 is a side perspective view of an absorbent garment having refastenable side seams.

Within the context of this specification, each term or phrase below will include the following meaning or meanings.

"Article" refers to a garment or other end-use article of manufacture.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Chassis web" or "garment chassis web" for purposes of the present invention refers to that portion of an in-process or finished absorbent article or garment exclusive of any non-integral side panels. A chassis web may be nonabsorbent, or absorbent with, or without, having specially adapted absorbent structures added thereto.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation. "Extensible" does not imply recovery of the original size or shape.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more desirably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "nonwettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Line of Weakness" is used to refer to a perforation, thinned area, nonpermanent or weak bond, or other means for facilitating separation of a material, a fabric or a layer of such material or fabric, whether defined by function or fabric type.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
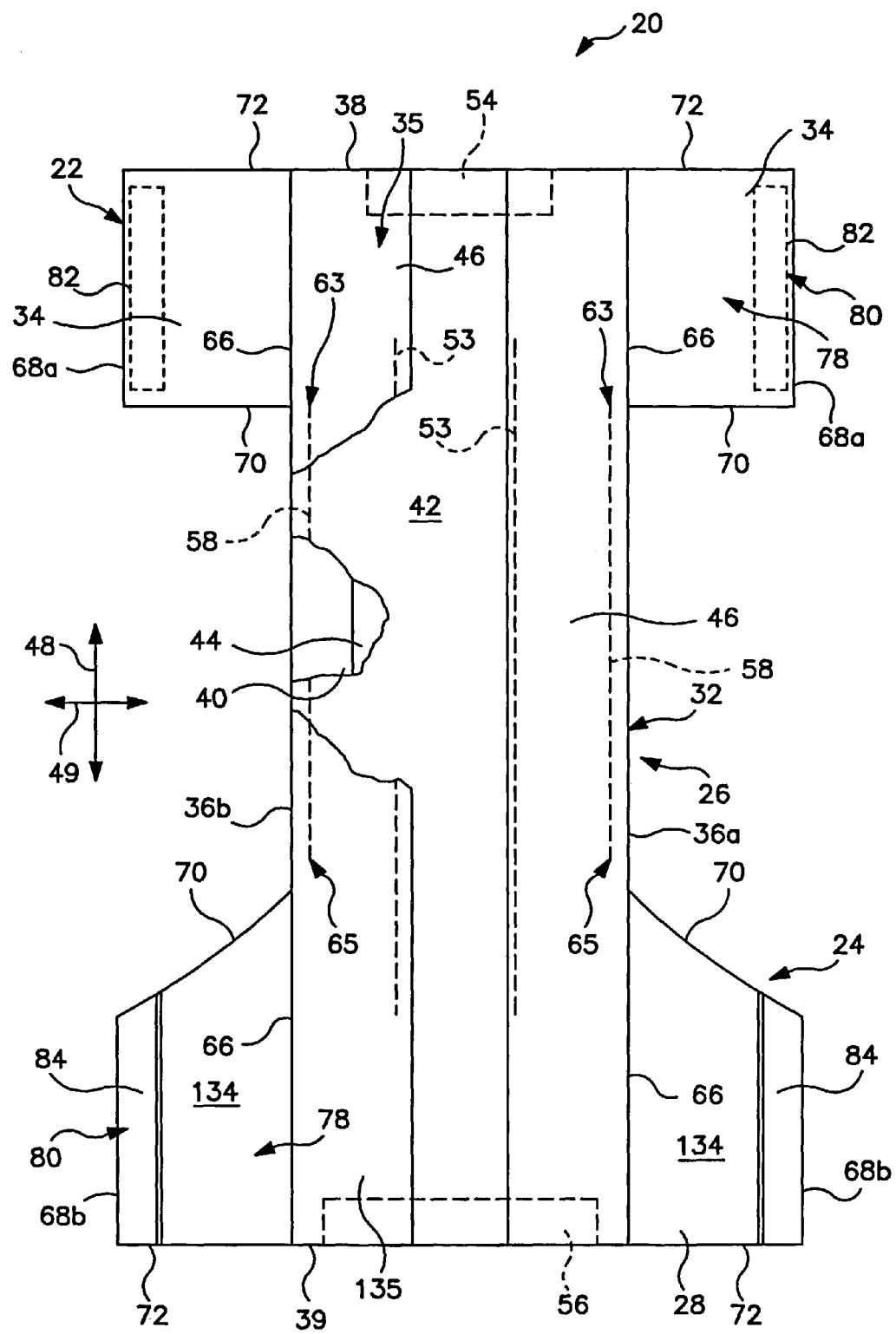
FIG. 3 is a plan view of an absorbent garment in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes directions depicted in FIG. 3. The longitudinal axis lies in the plane of the article and is generally parallel to a vertical plane that bisects a standing wearer into left and right body halves, when the article is worn. The transverse axis lies in the plane of the article generally perpendicular to the longitudinal axis. The article, although illustrated as longer in the longitudinal direction than in the transverse direction, need not be so.

"Machine direction" refers to the direction in which the web travels, as opposed to "cross direction" or "cross machine direction" which refers to the direction generally perpendicular to the machine direction.

"Melt blown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are desirably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

Words of degree, such as "Substantially", "About", and the like are used herein in the sense of "at, or nearly at, when given the manufacturing and material tolerances inherent in the stated circumstances" and are used to prevent the unscrupulous infringer from unfairly taking advantage of the invention disclosure where exact or absolute figures are stated as an aid to understanding the invention.

"Spunbond fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a nonsoftened condition when cooled to room temperature.

These terms may be defined with additional language in the remaining portions of the specification.

DETAILED DESCRIPTION OF THE PREFERRED EMBODIMENTS

The principles of the present invention can be incorporated into any suitable garment and especially disposable, or limited use garments. Examples of such suitable garments may include, but are not limited to, diapers, training pants, incontinence products, other personal care or health care garments, or the like. For ease of explanation, the description hereafter will be in terms of a child's training pant.

Figure 2:
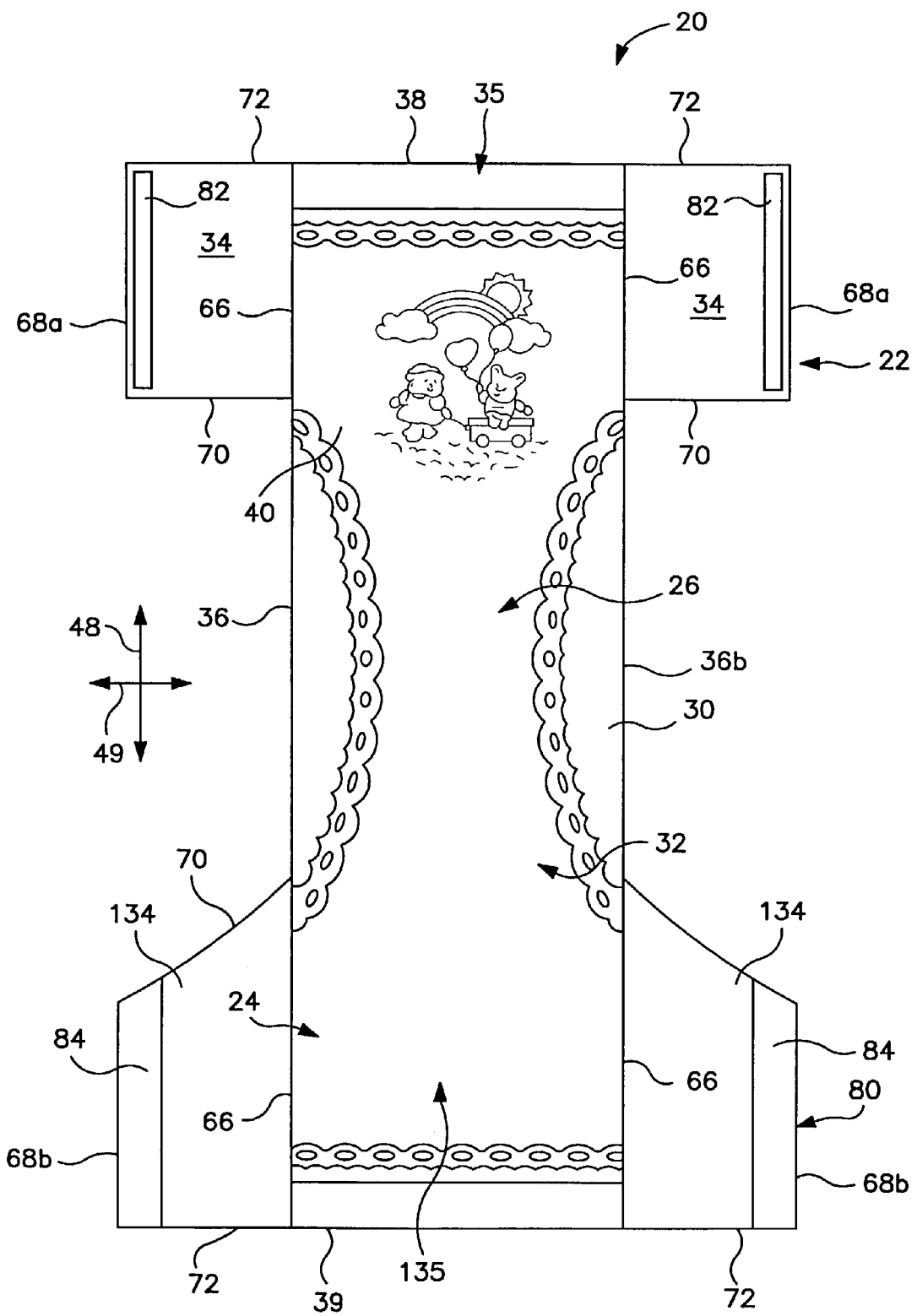
FIG. 2 is a plan view of an absorbent garment in a partially disassembled, stretched flat state, and showing the surface of the article that faces away from the wearer when the article is worn.

Referring to FIGS. 1-3, one such example is a disposable absorbent garment, such as a training pant 20, as illustrated for broad purposes of explanation of the environment of the present invention. The training pant 20 includes an absorbent chassis 32 and a fastening system 80. The absorbent chassis 32 helps define areas of the training pant including a front region 22, a back region 24, a crotch region 26 interconnecting the front and back regions, an inner surface 28 which is configured to contact the wearer, and an outer surface 30 opposite the inner surface which is configured to contact the wearer's clothing. The absorbent chassis 32 has a pair of transversely opposed side edges 36a, 36b and a pair of longitudinally opposed waist edges, which are designated front waist edge 38 and back waist edge 39. The front region 22 is contiguous with the front waist edge 38, and the back region 24 is contiguous with the back waist edge 39.

The illustrated absorbent chassis 32 may have a generally rectangular and absorbent composite structure, but may include other shapes such as those having leg cutouts, hour glass shapes, or other suitable shapes. Attached to the absorbent chassis 32 are a pair of transversely opposed front side panels 34, and a pair of transversely opposed back side panels 134. The absorbent chassis 32 and side panels 34 and 134 may include two or more separate elements. The illustrated absorbent chassis 32 desirably includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). Although illustrated as having an absorbent assembly the chassis structure of the present invention need not include any specially adapted absorbent structures. For reference, arrows 48 and 49 depicting the orientation of the longitudinal axis and the transverse axis directions, respectively, of the training pant 20 are illustrated in FIGS. 2 and 3.

With the training pant 20 in the partially fastened position as illustrated in FIG. 1, the side panels 34, 134 join the front and back regions 22, 24 including the front and back center panels 35, 135 together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the training pant 20 includes the transversely opposed front side panels 34 and a front center panel 35 (FIGS. 2 and 3) positioned between and interconnecting the side panels, along with a front waist elastic member 54 and any other connected components. The back region 24 of the training pant 20 includes the transversely opposed back side panels 134 and a back center panel 135 (FIGS. 2 and 3) positioned between and interconnecting the side panels 134, as well as a rear waist elastic member 56 and any other connected components. The waist edges 38 and 39 of the absorbent chassis 32 and waist end edges 72 of the side panels 34, 134 are configured to encircle the waist of the wearer when worn and provide the waist opening 50 which defines a waist perimeter dimension. Portions of the transversely opposed side edges 36a, 36b in the crotch region 26 and leg edges 70 of the side panels 34, 134 generally define the leg openings 52.

The training pant 20 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis 32 or may only extend partially along the length of the absorbent chassis 32. Suitable constructions and arrangements for the containment flaps 46 are generally well known to those skilled in the art and are described in U.S. Pat. No. 4,704,116 issued Nov. 3, 1987 to Enloe.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the transversely opposed side edges 36a, 36b and positioned in the crotch region 26 of the training pant 20. The leg elastic members 58 are desirably longitudinally aligned along the transversely opposed side edges 36a, 36b of the absorbent chassis 32. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may, but need not, have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbond web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL® N-62 from Hodgson Textile Chemicals of Mount Holly, N.C., U.S.A. and GLUCOPON® 220UP from Henkel Corporation of Ambler, Pa., in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) can be positioned between the outer cover 40 and the bodyside liner 42, which components can be joined together by any suitable means, such as adhesives, as is well known in the art. The absorbent assembly 44 can be any structure which is generally compressible, conformable, nonirritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 can be generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material can be present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can, if desired, also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the absorbent chassis 32 in the respective front and back regions 22 and 24, and are releasably attached to one another by a fastening system 80 when the training pant is worn. More particularly, as shown best in FIGS. 2 and 3, the front side panels 34 can be permanently bonded at, or proximal to, transversely opposed side edges 36a, 36b in the front region 22 along attachment lines 66, and the back side panels 134 can be permanently bonded at, or proximal to, to transversely opposed side edges 36a, 36b in the back region 24 along attachment lines 66. The side panels 34 and 134 may be attached using attachment means known to those skilled in the art such as adhesive, thermal, or ultrasonic bonding, or combinations thereof.

In particular embodiments for improved fit and appearance, the side panels 34 and 134 desirably have an average length dimension measured parallel to the longitudinal axis direction 48 that is about 20 percent or greater, and particularly about 25 percent or greater, of the overall length dimension of the absorbent article, also measured parallel to the longitudinal axis direction 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 in particular may have a continually decreasing length dimension moving from the attachment line 66 to a distal edge 68b of the back panel 134, as shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which can be folded over upon itself along an intermediate fold line (not shown).

The side panels 34 and 134 desirably include an elastic material capable of stretching in a direction generally parallel to the transverse axis direction 49 of the training pant 20. In particular embodiments, the front and back side panels 34 and 134 may each include an interior portion 78 disposed between the distal edge 68a, 68b and the respective front or back center panel 35 or 135. In the illustrated embodiment in FIG. 3, the interior portions 78 are disposed between the distal edges 68a, 68b and the transversely opposed side edges 36a, 36b of the absorbent chassis 32 The elastic material of the side panels 34 and 134 can be disposed in the interior portions 78 to render the side panels elastomeric in a direction generally parallel to the transverse axis. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis direction 49 and having a length from the attachment line 66 to the distal edge 68a, 68b and a width of about 2 centimeters, are all elastomeric.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No.

4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al. Alternatively, the side panel material may include other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIG. 1). The illustrated fastening system 80 includes fastening components 82 that are adapted to refastenably connect to mating fastening components 84. In one embodiment, one surface of each of the fastening components 82 and 84 includes a plurality of engaging elements that project from that surface. The engaging elements of the fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped, and may comprise a plurality of individual fastening elements or an entire surface of a side panel if so desired.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

Referencing FIGS. 4A, 4B, 4C, and 4D, a refastenable garment web 86 can be made from a garment chassis web 88 and at least a first side panel web 90, or first and second side panel webs 90 and 92, respectively. The chassis web 88 is desirably absorbent and may be suitably constructed with necessary material layers described above or as known in the art to produce an incontinence garment or the like. The chassis web 88 includes the inside or interior surface 28 to be placed against the skin of the wearer, and the outside or exterior surface 30 (see FIG. 6). As is known, the chassis web 88 is transported for manufacture with its longitudinal axis in, or defining, the machine direction 94 and a width 96 transverse thereto in the cross machine, or cross, direction 98 between first and second transversely opposed edges 36a, 36b, respectively.

Figure 6:
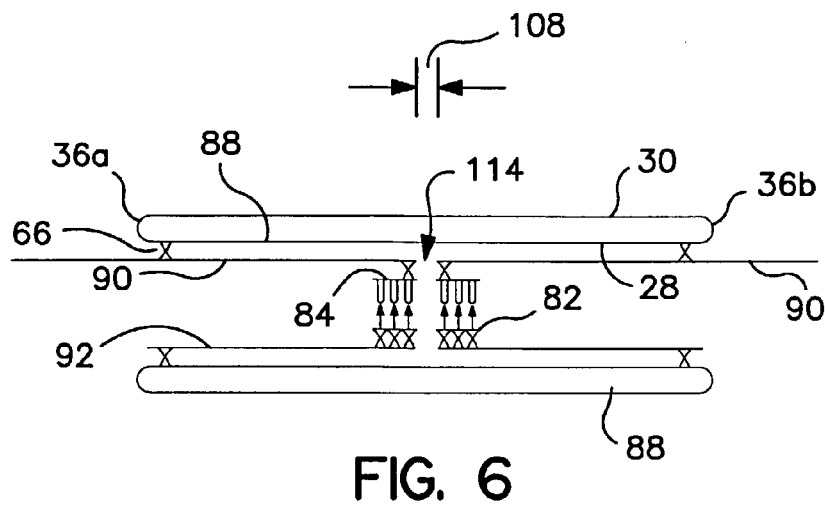
FIG. 6 shows a top, or end, view as seen at the waistband area of folded absorbent garment according to an embodiment of the present invention.
Figure 7:
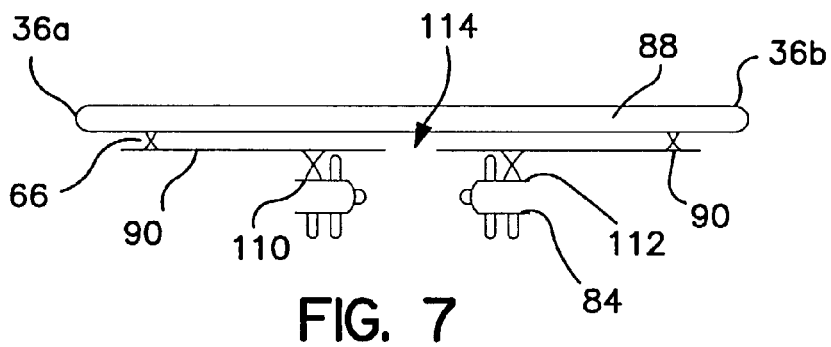
FIG. 7 illustrates the bonding and perforation of one fastening means to a side panel of the garment according to alternate embodiments of the present invention.

The first, or back, side panel web 90, comprising any suitable material, e.g., a spunbond laminate, as known in the art, desirably with stretch, or extensibility, in the transverse direction of the garment, here the cross direction 98, is laid over the interior surface 28 of the chassis web 88 and attached thereto, although attachment to the exterior surface 30 may be done. It will be appreciated that while the chassis web 88 is shown as having its transversely opposed side edges 36a, 36b conterminous, or congruent, with the side panel web, or webs, 90, 92, as at bond lines 66, there is no requirement for this condition. A side panel web, e.g. 90, may extend beyond the chassis web transversely opposed side edges 36a, 36b, or may lay within the transversely opposed side edges 36a, 36b, as shown in FIGS. 6 and 7, respectively, or may include combinations of the above arrangements within a single garment or within a single edge of a single garment. Once attached, the back side panel web 90 has a first, or waist, edge 72 which can be straight and, in the illustrative embodiment, a second, or leg end, edge 70, here shown as sinusoidal although other shapes, including straight, are possible. The first side panel waist edge 72 is desirably perpendicular with the transversely opposed side edges 36a, 36b of the chassis web 88.

Referencing FIGS. 4A and 4B, bonded to the back side panel web 90 are first fastener components, or strips, collectively 84. The first fastener strips 84 are represented as the loop portion of a cooperative hook and loop mechanical fastener system although other suitable fastening systems may be used. Hook and loop positions may also be reversed if desired. A carrier sheet or the like may also be used with the fastening components. In the alternative of FIG. 4B, the first side panel web 90 may be made as a material layer which will function as a loop fastener without need for the addition of separate loop fastener strips as indicated by their absence in FIG. 4B. The first fastener strips may extend the entire length of the first side panel web 90, i.e. along the machine direction 94, in the preferred embodiment. The second, sinusoidal, leg end edge 70 of course has varying dimensions with troughs 100 in the sinusoidal edge being closer to the first straight waist edge 72 and the crests 102 being farthest therefrom. The longitudinal axis 104, of the first fastener strip 84 is centered at the troughs 100 to allow the crests 102, or crest area, to provide a sufficient back, or rear, portion of the garment side panel for coverage of the buttock area of the wearer as will be appreciated upon a thorough understanding of the present invention.

The first side panel web 90, desirably with the fastener strip previously disposed thereon, can be connected, desirably with ultrasonic bonds and adhesives, along attachment lines 66, at, or proximal to, each chassis width edge 36a, 36b respectively, at either the interior or exterior surfaces of the chassis web 88.

Figure 8:
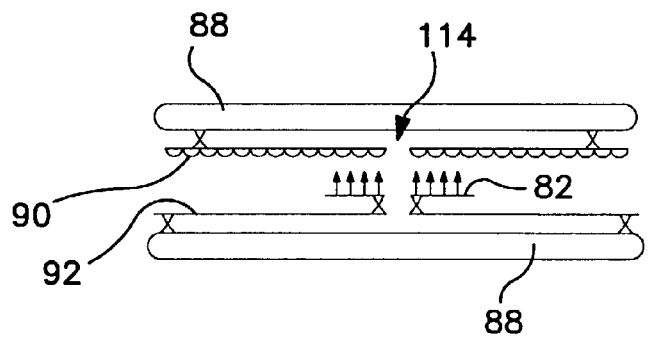
FIG. 8 illustrates an end view at the waistband area of a garment having a panel with one fastener component disposed on the entire surface thereof.

The first, or loop, fastener strip 84 can be adhered, or bonded, or otherwise disposed on the first side panel web 90 along its longitudinal axis 104 with a bond of a specified width 108 and left free at its peripheral edges 110, 112 to create a hinged attachment. The loops face up, or out of the plane of the paper in FIG. 4A, and away from the first side panel web 90. The width of the bond 108 can be then bisected by a through-cut or a line of weakness 114 extending through the thickness of the loop fastener and the underlying side panel web material (see FIGS. 6 and 7) to thereby create a pair of back side panels 134 upon separation of the one piece side panel web 90, as seen in FIG. 5, and more particularly in FIG. 6 where the loop fastener 84 has a hinged attachment to its panel 90. The loop fastener 84 is then free to assume a position placing the fastened hook and loop connection in a lap seam configuration when unfolded for wearing. As seen in FIG. 8, the above-described hinged fastener arrangement is particularly suitable for use with a fastening component 82 to be releasably attached to the surface of an opposing panel web 90 whose entire surface has disposed thereon the complementary fastener as per the embodiment of FIG. 4B.

Figure 4D:
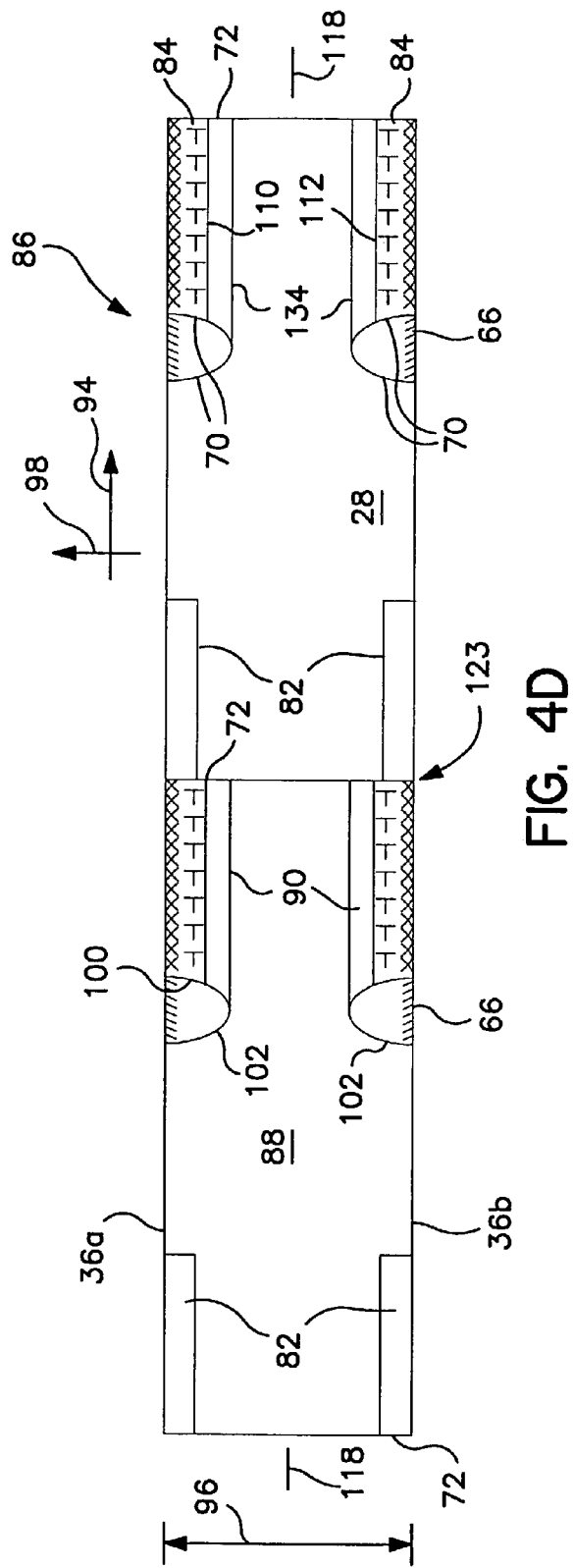
Figure 11:
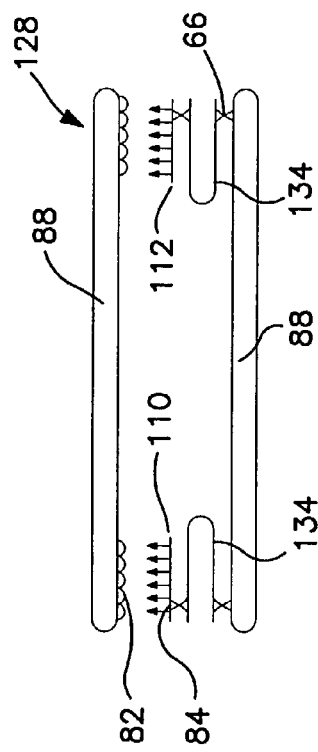
FIG. 11 illustrates an end view at the waistband area of a garment having a panel with one fastener component disposed on a limited area of the surface of the chassis web as in FIG. 4D.
Figure 5:
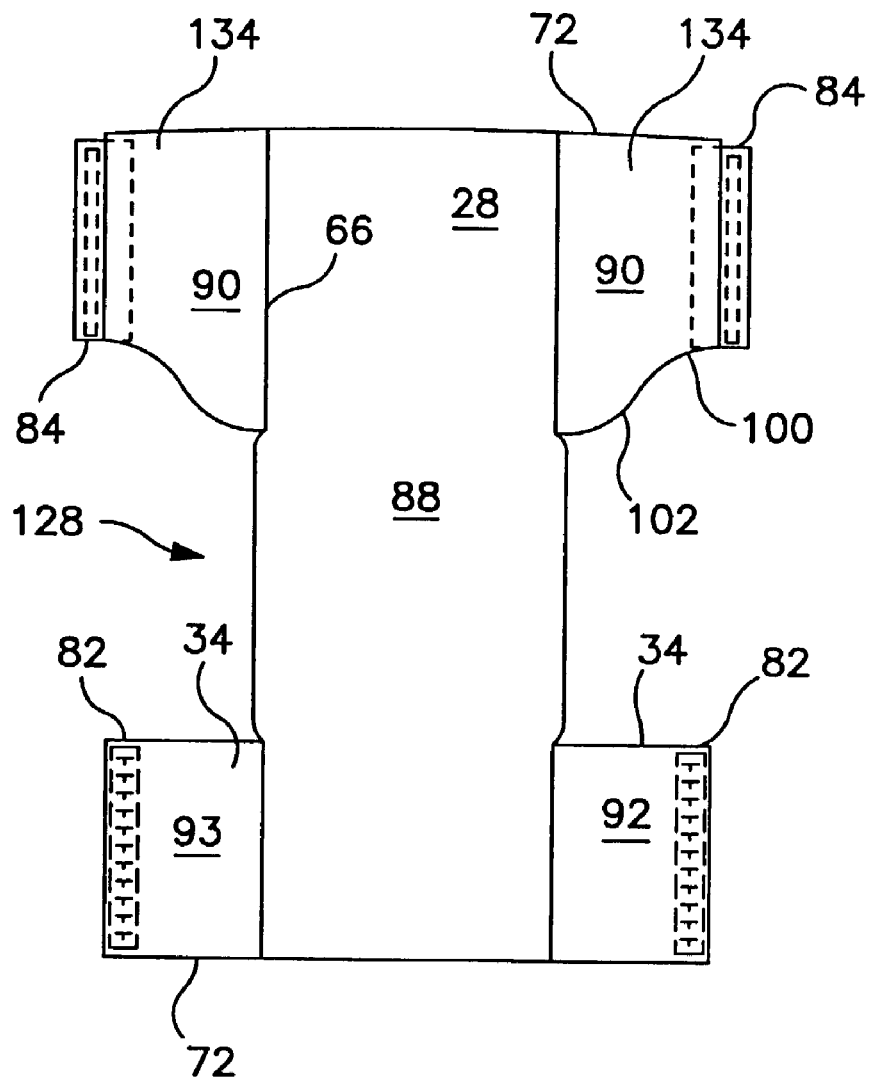
FIG. 5 shows the interior side of an individuated garment, unfolded, unfastened and fully laid out.

In the alternative of FIG. 4C, the first side panel web 90 may carry hook fastening components 84. The hook fastening components 84 are placed in opposition to a material layer integral with, or bonded to, the chassis interior surface 28 which will function as a loop fastener fastening component 82. The opposition of the fastening components 82, 84 is provided by a folding of the side panels 134, as made from the side panel web 90, to take hook fastening components 84 from their originally placed position proximal the longitudinal axis 118 and facing the interior surface 28, to a position proximal the chassis transversely opposed side edges 36a and 36b and facing away from the interior surface 28. Alternatively, referencing FIG. 4D, an arrangement of materials is shown similar to that of FIG. 4C except for the loop fastening components 82 being provided over a limited area, e.g., in strips proximal the transversely opposed side edges 36a and 36b and spaced in the machine direction 94 from the hook fastening components 84. The strips of the loop material 82 may be bonded to, or integral with, the inner surface 28 of the garment chassis web 86. FIG. 9 shows a waist edge end view of an individuated garment 128 made according the web of FIG. 4C and folded at its transverse midline to place the fastening components 82, 84 in proximity. The fastening components 84 are again noted as hingedly attached to the back side panels 134. FIG. 11 shows a waist edge end view of an individuated garment 128 made according the web of FIG. 4D and folded at its transverse midline to place the fastening components 82, 84 in proximity. The fastening components 84 are again noted as hingedly attached to the back side panels 134.

Alternatively, referencing FIG. 7, another arrangement securing a fastener strip 84 to a side panel web 90 and leaving it free to assume a lap seam configuration is shown. The fastener strip 84 may be bonded on the peripheral edges of its longitudinal direction 110, 112 with the exposed loop material facing the side panel web 90 and then separated as above and folded to place the exposed loop material 84 facing outwardly from the side panel web material.

The second, or front, side panel web 92, comprising any suitable material, and integral or separated from the first side panel web, can be laid over one, desirably the interior, surface 28 of the chassis web 88. Referencing FIG. 4B, if back and front side panel webs 90, 92, respectively, are provided as a single side panel web member 99, it will be appreciated that the single side panel web member 99 can be provided with a line of weakness in the cross direction 98 demarcating the side panel webs 90, 92 of consecutive garments. The front side panel web 92 can have a first, or waist edge 72 shown as straight and, as shown but not required, a shaped, or sinusoidal, second, leg end edge 70. The second side panel web leg end edge 70 is shown as a complementary sine curve whose crests 120 align with the front side panel web shaped edge troughs 100 across the chassis web longitudinal axis 118. The first and second side panel web shaped edges 70, may be conveniently cut from a single sheet of material if this is the case. Alternatively as seen in FIG. 4B, it can be acceptable to have a straight leg end edge 70 on the second, front, side panel 92. It will be appreciated that a front and back side panel may be applied to the web in a single unit and later individuated with their respective garments by a through-cut 123 through the web in the cross direction. The person of skill in the art will appreciate that the front and back waist edges 72, respectively, of two consecutive garments can be created by such a through-cut.

The front side panel web 92 can be then ultrasonically bonded with adhesive reinforcement or otherwise secured to the chassis web 88 at, or proximal to, each of the chassis web width edges 36a, 36b at attachment lines 66. Bonds of the side panels and fasteners are indicated by "x"s in FIGS. 6-9.

Second, mating fastener components or strips 82, indicated as hooks, are bonded to the front side panel web 92 at its crest points 120 so as to be placed opposite the corresponding loop strips 84 along the chassis web longitudinal axis 118. The hook fastener strip 82 and second side panel web 92 are likewise weakened or through-cut along the longitudinal axis 126 of each second fastener strip. The fastener strips 84, 82 are desirably in place on the side panel webs 90, 92, respectively, before the side panel webs are secured to the chassis web 88.

An individuated garment 128, separated from the garment web 86 by a single cut at line 123 along the cross direction, can then be folded, liner side in, at the garment transverse axis, to place the hook and loop fasteners in proximity or fastening opposition as shown in FIGS. 6, 8 and 9.

Figure 10:
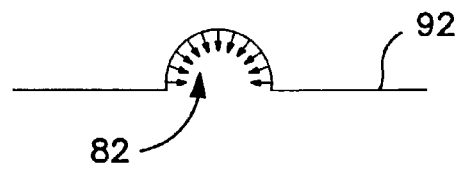
FIG. 10 shows a schematic end view of a folded side panel web which may be used with the present invention.

Referencing FIG. 10, a side panel web, e.g. 92, in some embodiments may comprise variously folded material, with or without fastener elements, e.g. 82, thereon in order to provide additional length to the side panels of the resultant garments within the scope of the present invention.

It will be appreciated that while the present invention has been described in terms of a single chassis web track traveling in the machine direction, efficiencies may be gained by practicing the teachings of the present invention in conjunction with multiple side-by-side tracks of chassis webs traveling in the machine direction.

While in the foregoing specification a compact, easily manufacturable, and desirably absorbent garment with refastenable side seams, and a method of making such a garment, has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A refastenable absorbent garment with a longitudinal axis in the machine direction, comprising:
   a. an absorbent chassis with a longitudinal axis in the machine direction and transversely opposed side edges;
   b. a discrete first side-panel web with a waist end edge and a leg end edge;
   c. a first fastener strip disposed on the discrete first side-panel web, the first fastener strip spanning substantially the length of the first side-panel web between the waist end edge and the leg end edge, wherein the fastener strip forms separable and refastenable side seams;
   d. the discrete first side-panel web with the first fastener strip thereon permanently bonded to the absorbent chassis at attachment lines proximal to each of the transversely opposed side edges of the absorbent chassis;

e. a discrete second side-panel web with a waist end edge and a leg end edge and having a second fastener complementary to the first fastener strip, the discrete second side-panel web permanently bonded to the absorbent chassis at attachment lines proximal to each of the transversely opposed side edges of the absorbent chassis;

f. whereby the discrete first side-panel web and the discrete second side-panel web lay mostly or entirely within the transversely opposed side edges of the absorbent chassis.

2. The refastenable absorbent garment with a longitudinal axis in the machine direction according to claim 1, further comprising a line of weakness or through-cut between the waist end edge and the leg end edge of the discrete first side panel web.

3. The refastenable absorbent garment with a longitudinal axis in the machine direction according to claim 1, further comprising a line of weakness or through-cut between the waist end edge and the leg end edge of the discrete second side panel web.

4. The refastenable absorbent garment with a longitudinal axis in the machine direction according to claim 1, further comprising: the garment being folded to place the first fastener strip in refastenable attachment with the second fastener strip.

5. A garment, comprising:
a. a garment chassis web with a longitudinal axis in the machine direction and opposed side edges in the cross machine direction;
b. a pair of discrete side panel webs permanently bonded to the garment chassis web only along attachment lines proximal to the opposed side edges of the chassis web and having disposed thereon a pair of complementary fastening components opposing each other in the machine direction, wherein the fastening components span substantially the machine-direction length of the side panels and form separable and refastenable side seams;
c. the pair of discrete side panel webs having a line of relative weakness in the machine direction
d. wherein the pair of discrete side panel webs lie mostly or entirely within the opposed side edges of the garment chassis web.

6. The refastenable absorbent garment with a longitudinal axis in the machine direction according to claim 1, further comprising a third fastener strip disposed on the discrete first side-panel web, the third fastener strip located between the waist edge and the leg end edge of the first side-panel web; and
a fourth fastener strip disposed on the discrete second side panel web, the fourth fastener strip located between the waist edge and the leg end edge of the second side-panel web and being complementary to the third fastener strip.

7. The refastenable absorbent garment with a longitudinal axis in the machine direction according to claim 1, wherein the discrete first and second side panel webs each comprise an average length dimension measured parallel to the longitudinal axis that is about 20 percent or greater than the overall length dimension of the absorbent article.

8. The refastenable absorbent garment with a longitudinal axis in the machine direction according to claim 1, wherein the discrete first and second side panel webs each comprise an average length dimension measured parallel to the longitudinal axis of about 10 centimeters or greater.

9. The refastenable absorbent garment with a longitudinal axis in the machine direction according to claim 1, wherein the discrete first and second side panel webs each comprise an elastic material.

10. The refastenable absorbent garment with a longitudinal axis in the machine direction according to claim 1, wherein the discrete first and second side panel webs each comprise a spunbond laminate.

11. The refastenable absorbent garment with a longitudinal axis in the machine direction according to claim 1, wherein the first fastener strip comprises hook type fasteners and the second fastener comprises loop type fasteners.

12. The refastenable absorbent garment with a longitudinal axis in the machine direction according to claim 11, wherein the material of the second side panel web functions as a loop type fastener.

13. The refastenable absorbent garment with a longitudinal axis in the machine direction according to claim 1, wherein the first fastener strip, the second fastener, or both are hingedly attached.

14. The refastenable absorbent garment with a longitudinal axis in the machine direction according to claim 1, wherein the discrete first and second side panel webs are cut from a single sheet of material and the leg end edge of the discrete first side panel web is complementary with the leg end edge of the discrete second side panel web.

15. The garment according to claim 5, wherein the pair of discrete side panel webs each comprise an average length dimension measured parallel to the longitudinal axis that is about 20 percent or greater than the overall length dimension of the absorbent article.

16. The garment according to claim 5, wherein the pair of discrete side panel webs each comprise an average length dimension measured parallel to the longitudinal axis of about 10 centimeters or greater.

17. The garment according to claim 5, wherein the pair of discrete side panel webs each comprise an elastic material.

18. The garment according to claim 5, wherein the pair of discrete side panel webs each comprise a spunbond laminate.

19. The garment according to claim 5, wherein the pair of complementary fastening components comprise hook and loop type fasteners.

20. The garment according to claim 19, wherein either or both of the pair of complementary fastening components are hingedly attached.

* * * * *